(12) United States Patent
Kissel et al.

(10) Patent No.: US 8,003,734 B2
(45) Date of Patent: Aug. 23, 2011

(54) BIOLOGICALLY TOLERATED LOW MOLECULAR WEIGHT POLYETHYLENIMINES

(75) Inventors: Thomas Kissel, Marburg (DE); Dagmar Fischer, Marburg (DE); Hans-Peter Elsässer, Marburg (DE); Thorsten Bieber, Niederaula (DE)

(73) Assignee: Sanofi-Aventis Deutschland GmbH (DE)

(*) Notice: Subject to any disclaimer, the term of this patent is extended or adjusted under 35 U.S.C. 154(b) by 962 days.

(21) Appl. No.: 10/265,539

(22) Filed: Oct. 7, 2002

(65) Prior Publication Data

US 2003/0027784 A1 Feb. 6, 2003

Related U.S. Application Data

(63) Continuation of application No. 09/667,932, filed on Sep. 22, 2000, now abandoned, which is a continuation of application No. 09/162,101, filed on Sep. 28, 1998, now abandoned.

(30) Foreign Application Priority Data

Sep. 30, 1997 (DE) .................................. 197 43 135

(51) Int. Cl.
*C08G 73/02* (2006.01)
(52) U.S. Cl. ........................................................ 525/417
(58) Field of Classification Search .................. None
See application file for complete search history.

(56) References Cited

U.S. PATENT DOCUMENTS

| | | | | |
|---|---|---|---|---|
| 2,182,306 A * | 12/1939 | Ulrich et al. | ................... | 548/967 |
| 4,032,480 A * | 6/1977 | Zhuk et al. | .................... | 528/424 |
| 4,690,985 A | 9/1987 | Tomalia et al. | ................ | 525/419 |
| 5,714,166 A | 2/1998 | Tomalia et al. | ................ | 424/486 |
| 5,830,730 A | 11/1998 | German et al. | ................ | 435/455 |
| 5,916,803 A | 6/1999 | Sedlacek et al. | | |
| 5,919,442 A | 7/1999 | Yin et al. | .................... | 424/78.18 |
| 5,977,307 A | 11/1999 | Friden et al. | ................... | 530/350 |
| 6,013,240 A * | 1/2000 | Behr et al. | .................... | 424/1.21 |
| 6,036,955 A | 3/2000 | Thorpe et al. | ............... | 424/136.1 |

FOREIGN PATENT DOCUMENTS

| DE | 2530042 A1 * | 1/1977 |
|---|---|---|
| DE | 19649645.4 | 6/1998 |
| EP | 0790312 A2 | 8/1997 |
| EP | 0 846 772 | 6/1998 |
| WO | WO 96/02655 | 2/1996 |

OTHER PUBLICATIONS

Gembitskii, P.A. et al., "The polymerization of ethylenimine to give linear polyethylenimine", Yysokomol. Soyed A20: No. 7, 1505-1510, 1978. English Language Abstract Only.
Abdallah et al, Hum. Gene Ther., vol. 7, 1996, pp. 1947-1954.
Behr, Bioconjugate Chem., vol. 5, 1994, pp. 382-389.
Behr, Chimia, vol. 51, 1997, pp. 34-36.
Boussif et al., Gene Therapy, vol. 3, 1996, pp. 1074-1080.
Boussif et al., Proc. Natl. Acad. Sci., vol. 92, 1995, pp. 7297-7301.
Cherng et al., Pharm. Res., vol. 13, No. 7, 1996, pp. 1038-1042.
Choksakulnimitr et al., J. Control. Rel., vol. 34, 1995, pp. 233-241.
Cotten et al., Meth. In Enzymol., vol. 217,1993, pp. 618-644.
Crystal, Science, vol. 270, 1995, 404-410.
Dick et al., J. Macromol. Sci., vol. A4, 1970, pp. 1301-1314.
Gao et al, Gene Therapy, vol. 2, 1995, pp. 710-722.
Godbey et al. (J. Biomedical Materialsa Research, 45, 3, pp. 268-275.
Gopal, Mol. Cell. Biol., vol. 5, 1985, pp. 1188-1193.
Haensler et al., Bioconjugate Chem., vol. 4, 1993, pp. 372-379.
Ledley, Human Gene Therapy, vol. 6, 1129-1144, 1995.
Midoux et al., Nucleic Acids Research, vol. 21, No. 4, 1993, pp. 871-878.
Miller, Nature, vol. 357, 1992, pp. 455-460.
Mischeck et al., Cell. Tiss. Res., vol. 256, 1989, pp. 221-226.
Mulligan, Science, vol. 260, 1993, pp. 926-932.
Remy et al., J. Lip. Res., vol. 6, No. 3, 1996, 535-544.
Tomlinson et al., J. of Contr. Rel., vol. 39, 1996, pp. 357-372.
Trubetskoy et al., Bioconjugate Chem., vol. 3, 1992, pp. 323-327.
Verma et al. (Nature, vol. 389, 18, pp. 239-242).
Vollmert, Grudiss der Makromdekularen Chemie, Springer Verlag Berlin, 1962, pp. 216-225.
Wagner et al., Proc. Natl. Acad. Sci., vol. 87, 1990, pp. 3410-3414.
Weaker, JACS, vol. 57, 1935, pp. 2328-2329.
Wolfert et al., Hum. Gene Ther., vol. 7, 1996, pp. 2123-2133.
Wu et al., Biotherapy, vol. 3, 1991, pp. 87-95.
Wu et al., J. Biol. Chem., vol. 262, No. 10, 1987, pp. 4429-4432.
Zenke et al., Proc. Natl. Acad. Sci., vol. 87, 1990, pp. 3655-3659.

* cited by examiner

*Primary Examiner* — Doug Schultz
(74) *Attorney, Agent, or Firm* — Frommer Lawrence & Haug LLP

(57) ABSTRACT

The invention relates to low molecular weight polyethylenimines, to vectors for inserting nucleic acids into cells which contain low molecular weight polyethylenimines, and to the preparation and use of the low molecular weight polyethylenimine and the vector.

The invention relates to a vector for inserting a nucleic acid into a cell, which vector contains a low molecular weight polyethylenimine (LMW PEI) and a nucleic acid, with the LMW PEI having a molecular weight of less than 50,000 Da.

8 Claims, No Drawings

BIOLOGICALLY TOLERATED LOW MOLECULAR WEIGHT POLYETHYLENIMINES

This application is a continuation of U.S. application Ser. No. 09/667,932, filed on 22 Sep. 2000, now abandoned, which is a continuation of U.S. application Ser. No. 09/162,101, filed on 28 Sep. 1998, now abandoned.

This application claims priority of DE 197 43 135.6 filed Sep. 30, 1997, the disclosure of which is hereby incorporated by reference.

The invention relates to low molecular weight polyethylenimines, to vectors which contain low molecular weight polyethylenimines for inserting nucleic acid into cells, and to the preparation and use of the low molecular weight polyethylenimine and the vector.

The therapeutic administration of DNA in vivo has not so far led to any significantly successful therapy in human clinical studies. The reasons for this are to be found, in particular, in the low efficiency of gene transfer, the limited expression of the genetic information [Cotton et al., Meth. Enzymol. 217: 618-644 (1993)] and the insufficient biocompatibility [Choksakulnimitr et al., J. Control Rel. 34: 233-241 (1995)] of the cationic carrier materials employed. Although viral vectors, such as retroviruses [Miller, Nature 357: 455-460 (1992)] or adenoviruses [Mulligan, Science 260: 926-932 (1993)], gave very promising results in vitro, their use in vivo was limited, particularly because of their inflammatory and immunogenic properties and the danger of mutagenesis and integration into the genome of the cell [Crystal, Science 270: 404-410 (1995)]. Nonviral vectors, which are not only simpler to handle than viral systems but are also able to funnel DNA into cells in a reliable and efficient manner, offered a possible alternative [Tomlinson and Rolland, J. Contr. Rel. 39: 357-372 (1996)].

Over the course of time, synthetic vectors based on water-soluble, cationic polymers such as poly-L-lysine (PLL) [Wu and Wu, Biotherapy 3: 87-95 (1991)], DEAE-dextran [Gopal, Mol. Cell. Biol. 5: 1183-93 (1985)], dendrimers [Haensler and Szoka, Bioconjugate Chem. 4: 372-379 (1993)] or cationic methacrylic acid derivatives [Wolfert et al., Hum. Gene Ther. 7: 2123-2133 (1996)] have been developed as an alternative to the classical form of transfection, i.e. "lipofection" using cationic lipids [Gao and Huang, Gene therapy 2: 710-722 (1995)] and amphiphilic substances [Behr, Bioconjugate Chem. 5: 382-389 (1994)]. The crucial advantage of "polyfection" using cationic polymers consists in the infinitely large number of possible structural variations which are able to influence the physicochemical and biological properties of the polymers, and their plasmid/polymer complexes, in the desired manner. It has been possible to increase the efficiency of these vectors substantially by additionally coupling cell-specific ligands such as transferrin [Wagner et al., Proc. Natl. Acad. Sci. 87: 3410-3414 (1990)], asialoglycoprotein [Wu and Wu, J. Biol. Chem. 262: 4429-4432 (1987)], and various antibodies [Trubetskoy et al., Bioconjugate Chem. 3: 323-327 (1992)] and carbohydrates [Midoux et al., Nucleic Acid Research 21: 871-878 (1993)].

In a large number of different adherent and suspension cell lines, polyethylenimine (PEI), which is a cationic polymer which has a three-dimensional, branched structure, has led to transfection rates which are in some cases above average in magnitude [Boussif et al., Gene Therapy 3: 1074-1080 (1996)]. For example, 95% transformation of 3T3 fibroblasts has been achieved in vitro. The PEI-mediated transfer of genes into the mouse brain in vivo resulted in a long-term expression of reporter genes and the Bcl2 gene in neurons and glia cells which is of the same order of size as in the case of adenoviral gene transfer [Abdallah et al., Hum. Gene Ther. 7: 1947-1954 (1996)].

Polyethylenimine possesses outstanding properties as compared with other polycations which are known from the literature, such as PLL [Zenke et. al., Proc. Natl. Acad. Sci. 87: 3655-3659 (1990)], methacrylate derivatives [Cherng et al., Pharm. Res. 13: 1038-1042 (1996)] or DEAE-dextran [Gopal, Mol. Cell. Biol. 5: 1183-93 (1985)]. As a result of its crosslinked structure and high charge density, it is able to condense and complex plasmids to a high degree. DNA can then be funneled into cells in the form of these complexes. The mechanisms involved in the uptake, the intracellular processing and the lysotropic activity of the PEI/plasmid complexes have not so far been finally clarified.

The crucial advantage of the PEI appears to be a pH-dependent change in its structure which leads to the destabilization of endosomal/lysosomal compartments and thereby facilitates release of the complexes into the cytoplasm. In particular, it is thought that the amino functions of the molecule, which have different pKa values, are responsible for the PEI having a pronounced buffering capacity ("proton sponge") which leads, in association with acidification of the endosomes, to protonation and consequent swelling of the polymers and thereby to rupture of the vesicle membranes. The inflow of protons which is mediated by the endosomal ATPase presumably gives rise at the same time to the passive influx of anionic chlorides which, in the presence of PEI, leads to a massive increase in total ion concentration and consequently to osmotic swelling of the endosomes [Behr, Chimia 51: 34-36 (1997)]. For this reason, lysosomotropic agents such as chloroquine, which are essential for transfecting PLL, for example, have no influence on the rate at which the PEIs are transfected [Remy and Behr, J. Lip. Res. 6: 535-544 (1996)].

WO 9602655 A1 described the use of high molecular weight polyethylenimine, having a molecular weight of 50 kDa and 800 kDa (molar mass 50,000 g/mol and 800,000 g/mol, respectively), for transfecting DNA into cells.

According to information supplied by the manufacturer (e.g. Fluka, Neu Ulm) commercially obtainable PEI has a molecular weight of 600-1000 kDa. Such high molecular weight PEI preparations (HMW PEI) are markedly cytotoxic at a concentration of 0.01 mg/ml and above and after a short incubation of 3 h. In addition, the polyethylenimine structure cannot be cleaved either enzymically or hydrolytically and is consequently not biologically degradable. Furthermore, HMW PEI can presumably not be excreted either via the feces or via the kidneys.

As a consequence, the in-vivo administration of the HMW PEI which has thus far been used, for example within the context of gene therapy, is associated with substantial risks.

The invention relates to a polyethylenimine which has a molecular weight of less than 50,000 Da, preferably between 500 Da and 30,000 Da (low molecular weight PEI: LMW PEI), to the method (or the process) for preparing this LMW PEI and to the use of LMW PEI in a complex with viral and nonviral nucleotide sequences or nucleic acids for inserting nucleotide sequences into a cell, to the administration of this cell to a mammal for achieving the prophylaxis or therapy of a disease, and to the administration of LMW PEI in a complex with a nucleotide sequence to a mammal for achieving the prophylaxis or therapy of a disease.

The present invention relates to a vector which contains a low molecular weight polyethylenimine (LMW PEI) and a nucleic acid (nucleotide sequence), with the LMW PEI having a molecular weight of less than 50,000 Da. In particular, the invention relates to vectors for inserting nucleic acid constructs into a cell, with the vectors containing complexes which are composed of polyethylenimine having a molecular weight of less than 50,000 Da and nucleic acids which are preferably nonviral or viral nucleic acid constructs.

Preferably, the LMW PEI has a molecular weight of from 500 to 30,000 Da. In a preferred embodiment of the invention, the LMW PEI has a molecular weight of from 1000 to 5000 Da. Particular preference is given to a molecular weight of about 2000 Da.

The invention relates to a vector which contains a low molecular weight polyethylenimine and a nucleic acid, with the LMW PEI being prepared by polymerizing monomeric ethylenimine in aqueous solution by means of adding hydrochloric acid, with the aqueous solution preferably being from 0.1% strength to 90% strength with respect to monomeric ethylenimine and from 0.1% strength to 10% strength with respect to concentrated hydrochloric acid (37% strength).

The invention relates to a vector which contains a low molecular weight polyethylenimine and a nucleic acid, with the LMW PEI not exhibiting any turbidity or precipitation in swelling studies carried out in 0.1 M phosphate buffer at different pH values in the range from pH 4 to pH 10.

The invention relates to a vector which contains a low molecular weight polyethylenimine and a nucleic acid, with transfection rates which are greater than 1%, preferably transfection rates of 5% or more and, in special embodiments, transfection rates of 10% or more, being achieved when this vector is used.

The nucleic acid, can, for example, be a DNA or an RNA. The nucleic acid can be an oligonucleotide or a nucleic acid construct. The nucleic acid is preferably a viral or nonviral nucleic acid construct. The nucleic acid construct is preferably a gene or a plasmid. The nucleic acid construct can contain a transgene. The nucleic acid construct can contain one or more effector genes. An effector gene can, for example, encode a pharmacological active compound or its prodrug form and/or encode an enzyme. The nucleic acid construct is preferably configured such that the gene (e.g. effector gene or transgene) is expressed specifically, for example virus-specifically (i.e., e.g. only in virus-infected cells), (target)-cell-specifically, specifically in relation to metabolism, cell-cycle-specifically, specifically in relation to development, or else non-specifically. In the simplest case, the nucleic acid contains a gene, which encodes the desired protein, and specific promotor sequences and, where appropriate, further regulatory sequences. Viral promotor sequences and/or enhancer sequences can, for example, be present for the purpose of augmenting and/or extending the expression of the gene. Promotor sequences and/or enhancer sequences of this nature are reviewed, for example, in Dillon, TiBTech 11, 167 (1993). Examples of these sequences are the LTR sequences of Rous sarcoma viruses and of retroviruses, the promoter and enhancer regions of CMV viruses, the ITR sequences and/or promotor sequences p5, p19 and p40 of MV viruses, the ITR and/or promotor sequences of adenoviruses, the ITR and/or promotor sequences of vaccinia viruses, the ITR and/or promotor sequences of herpesviruses, promotor sequences of parvoviruses and the promotor sequences (upstream regulator region) of papillomaviruses.

The LMW PEI is complexed with the nucleic acid by the two starting substances being mixed. Preference is given to selecting a mixing ratio which leads to complexes which have a neutral or cationic charge. Preference is given to the vector being composed of complexes which contain more than 50% (% by weight) of LMW PEI. The vector preferably exhibits a ratio by weight of LMW PEI to nucleic acid of 3:1 or more, particularly preferably of 5:1 or more or of 8:1 or more.

An effector gene can be expressed together with a ligand as a fusion protein, for example if, in addition to the sequence of the effector gene, the nucleic acid construct also contains a sequence which encodes a ligand.

In a quite general manner, the invention relates to a vector which contains an LMW PEI, a nucleic acid and, where appropriate, a ligand. The individual components for the vector are preferably linked covalently and/or by means of adsorptive bonds. For example, the encoded protein and/or the LMW PEI can be coupled to a ligand. In particular, the invention relates to vectors in which the low molecular weight polyethylenimine is coupled to a cell-specific (or target-cell-specific) ligand.

The ligand is preferably a cell-specific or target-cell-specific ligand. A target-cell-specific ligand can bind to the outer membrane of a target cell, preferably an animal or human target cell. A target-cell-specific ligand exhibits a high specificity for the target cell. A vector which contains a target-cell-specific ligand can be used for the target-cell-specific transfer of a nucleic acid. The target cell can, for example, be an endothelial cell, a muscle cell, a macrophage, a lymphocyte, a glia cell, an hematopoietic cell, a tumor cell, e.g. a leukemia cell, a virus-infected cell, a bronchial epithelial cell or a liver cell, e.g. a sinusoidal cell of the liver.

A ligand which binds specifically to endothelial cells can, for example, be selected from the group which consists of monoclonal antibodies, or their fragments, which are specific for endothelial cells, glycoproteins which carry mannose terminally, glycolipids or polysaccharides, cytokines, growth factors, adhesion molecules, or, in a particularly preferred embodiment, of glycoproteins from the envelope of viruses which have a tropism for endothelial cells. A ligand which binds specifically to smooth muscle cells can, for example, be selected from the group which consists of monoclonal antibodies, or their fragments, which are specific for actin, cell membrane receptors and growth factors, or, in a particularly preferred embodiment, of glycoproteins from the envelope of viruses which have a tropism for smooth muscle cells. A ligand which binds specifically to macrophages and/or lymphocytes can, for example, be selected from the group which consists of monoclonal antibodies which are specific for membrane antigens on macrophages and/or lymphocytes, intact immunoglobulins or Fc fragments of polyclonal or monoclonal antibodies which are specific for membrane antigens on macrophages and/or lymphocytes, cytokines, growth factors, peptides which carry mannose terminally, proteins, lipids or polysaccharides, or, in a particularly preferred embodiment, of glycoproteins from the envelope of viruses, in particular the influenza C virus HEF protein having a mutation in nucleotide position 872 or influenza C virus HEF cleavage products which contain the catalytic triad serine 71, histidine 368 or 369 and aspartic acid 261. A ligand which binds specifically to glia cells can, for example, be selected from the group consisting of antibodies, and antibody fragments, which bind specifically to membrane structures of glia cells, adhesion molecules, peptides which carry mannose terminally, proteins, lipids or polysaccharides, growth factors, or, in a particularly preferred embodiment, of glycoproteins from the envelope of viruses which have a tropism for glia cells. A ligand which binds specifically to hematopoietic cells can, for example, be selected from the group consisting of antibodies, or antibody fragments, which are specific for a stem cell factor receptor, IL-1 (in particular receptor type 1 or 11), IL-3 (in particular receptor type a or β), IL-6 or GM-CSF, and also intact immunoglobulins or Fc fragments which exhibit this specificity and growth factors, such as SCF, IL-1, IL-3, IL-6 or GM-CSF, and their fragments, which bind to the affiliated receptors. A ligand which binds specifically to leukemia cells can, for example, be selected from the group consisting of antibodies, antibody fragments, immunoglobulins or Fc fragments which bind specifically to membrane structures on leukemia cells, such as CD13, CD14, CD15, CD33, CAMAL, sialosyl-Le, CD5, CD1e, CD23, M38, IL-2 receptors, T cell receptors, CALLA or CD19, and also growth factors or fragments derived therefrom or retinoids. A ligand which binds specifically to virus-infected cells can, for example, be selected from the group consisting of antibodies, antibody fragments, intact immunoglobulins or Fc fragments which are specific for a virus antigen which, after infection by the virus, is expressed on the cell membrane of the infected cell. A ligand which can bind specifically to bronchial epithelial cells, sinusoidal cells of the liver or liver cells can, for example, be selected from the group consisting of transferrin, asialoglycoproteins, such as asialoorosomucoid, neoglycoprotein or galactose, insulin, peptides which carry mannose terminally, proteins, lipids or polysaccharides, intact immunoglobulins or Fc fragments which bind specifically to the target cells, and, in a particularly preferred embodiment, of glycoproteins from the envelope of viruses which bind specifically to the target cells. Other detailed examples of ligands are disclosed, for example, in EP 0 790 312 and EP 0 846 772.

The invention furthermore relates to a process for preparing a low molecular weight, cationic, polyethylenimine (PEI)-based polymer conjugate (LMW PEI) by means of the ring-opening polymerization of aziridine (monomeric ethylenimine).

In this context, the ethylenimine is preferably prepared from ethanolamine by the method of Wenker (JACS 57: 2328 (1935)). The boiling point is preferably 55.0-56.0° C.

German patent application 665,791 (1938) describes the synthesis of PEI by adding catalysts such as acids or boron trifluoride to liquid, monomeric ethylenimine. In accordance with the invention, monomeric ethylenimine is polymerized in aqueous solution in the added presence of hydrochloric acid, in analogy with Dick et al., J.Macromol. Sci. A4: 1301-1314 (1970).

For the polymerization, a 0.1% strength to 90% strength ethylenimine (monomer) solution in distilled water is prepared with stirring and from 0.1% to 10% concentrated hydrochloric acid (37%) is added as catalyst. The polymerization is carried out over 1-30 days, preferably 4 days, at a temperature of 30-70° C., preferably 50° C.

The polymers are characterized, for example, by means of $^{13}$C-NMR spectroscopy, size-exclusion chromatography, light scattering and/or viscosimetry. The process for determining molecular weight using the light scattering method is described in principle in B. Vollmert (1962) "Grundriss der Makromolekularen Chemie (Outline of macromolecular chemistry)", Springer Verlag, Berlin, pages 216-225. The molecular weight determination is preferably carried out by means of the light scattering method, in particular laser scattered light measurement, e.g. using a dispersion photometer, e.g. a Wyatt Dawn DSP dispersion photometer at 633 nm following direct injection into a K5 measuring cell. The molecular weight can, for example, be determined using calibration constants which are determined in toluene and the known initial sample weight.

The described process can be used to prepare low molecular weight PEI (LMW PEI) having molecular sizes of between 500 Da and 50,000 Da. The molecular weight of the low molecular weight PEI (LMW PEI) is therefore markedly lower than that of the HMW PEI and markedly lower than the renal threshold of 50 kDa, which means that renal elimination should be ensured.

Surprisingly, it emerged that LMW PEI is markedly superior to HMW PEI with regard to its effectiveness as a vector for inserting nucleic acids or nucleic acid constructs into cells and with regard to its biological tolerability. LMW PEI having molecular sizes between 1000 Da and 30,000 Da proved to be most suitable. LMW PEI is able to bind, condense and increase the positive nature of DNA. When complexed with DNA containing a reporter gene, LMW PEI having a molecular weight of, for example, about 2000 Da gave rise [in the presence of serum] to levels of reporter gene expression in mammalian cells [for example in mouse fibroblasts (3T3) and human endothelial cells (ECV 304)], which were 100-fold higher than those achieved with commercial high molecular weight (HMW) PEI. At the same time, the cytotoxicity of the LMW PEI for fibroblasts was markedly reduced as compared with that of HMW PEI.

The invention consequently relates to polyethylenimine which has a molecular weight of less than 50,000 Da, preferably of between 500 Da and 30,000 Da (LMW PEI), to the method for preparing this LMW PEI and the use of LMW PEI in a complex together with viral and nonviral nucleotide sequences for inserting nucleotide sequences into a cell, to the administration of this cell to a mammal for the purpose of achieving the prophylaxis or therapy of a disease, and to the administration of LMW PEI in a complex with a nucleotide sequence to a mammal for the purpose of achieving the prophylaxis or therapy of a disease.

The invention relates to a low molecular weight polyethylenimine which has a molecular weight of less than 50,000 Da, preferably to LMW PEI which is prepared by the process described.

The invention also relates to the use of LMW PEI which has a molecular weight of less than 50,000 Da, preferably 1000-30,000 Da, in particular about 2000 Da. The LMW PEI can, for example, be used for inserting a nucleic acid into a cell, for preparing a vector for inserting a nucleic acid into a cell or for preparing a pharmaceutical and/or in gene therapy.

The invention furthermore relates to a process for preparing a vector for inserting a nucleic acid into a cell. The vector can, for example, be prepared by mixing an appropriate quantity of LMW PEI with an appropriate quantity of nucleic acid. The LMW PEI and the nucleic acid are preferably mixed in an aqueous solution.

The invention furthermore relates to the use of the vector. For example, the vector can be used for inserting a nucleic acid into a cell or a target cell (transfection or polyfection), or for preparing a pharmaceutical and/or in gene therapy. The invention preferably relates to the use of the vector for inserting nonviral or viral nucleic acid constructs into a cell and to the administration of this (transfected) cell to a patient for the purpose of achieving the prophylaxis or therapy of a disease, with it being possible for the cell to be, for example, an endothelial cell, a lymphocyte, a macrophage, a liver cell, a fibroblast, a muscle cell or an epithelial cell, and it being possible for this cell to be injected, for example locally onto the skin, subcutaneously, intramuscularly, into a wound, into a body cavity, into an organ or into a blood vessel. In another preferred embodiment, the invention relates to the use of the vector for achieving the prophylaxis or therapy of a disease, with it being possible, for example, for the vector to be injected locally onto the skin, subcutaneously, intramuscularly, into a wound, into a body cavity, into an organ or into a blood vessel.

The LMW PEI, or a vector which contains the LMW PEI, can, for example, be used for inserting a nucleic acid into a cell/target cell, with the cell/target cell being an endothelial cell, a lymphocyte, a macrophage, a liver cell, a fibroblast, a muscle cell or an epithelial cell.

The invention furthermore relates to a process for preparing a transfected cell or target cell, with the LMW PEI and/or the vector being incubated with this cell. The transfection is preferably carried out in vitro. The invention also relates to a transfected cell or target cell which contains LMW PEI and/or a novel vector. The invention furthermore relates to the use of the transfected cell, for example as a pharmaceutical and/or for preparing a pharmaceutical and/or for gene therapy.

The invention furthermore relates to a pharmaceutical which comprises an LMW PEI and/or a novel vector and/or a transfected cell. The invention also relates to a process for preparing a pharmaceutical, with a nucleic acid being mixed with an LMW PEI and, where appropriate, further additives.

Since the novel LMW PEI is less strongly branched than HMW PEI, and therefore contains more amino groups than does HMW PEI, there is a far greater opportunity to couple the LMW PEI, as compared with the HMW PEI, to a cell-specific ligand. The invention consequently relates to the coupling of the LMW PEI to a cell-specific ligand and to the use of the coupling product, in a complex with a viral or nonviral nucleotide sequence, for inserting the nucleotide sequence into a cell or for administering the complex to a mammal for achieving the prophylaxis or therapy of a disease. Patent applications EP97101506.0 and DE19649645.4 have already described the possibilities of preparing and coupling cell-specific ligands in detail. These patent applications are hereby expressly incorporated by reference.

Complexes beween LMW PEI, where appropriate coupled to a cell-specific ligand, and a viral or nonviral nucleic acid construct constitute a vector for gene therapy. In a preferred embodiment, these vectors are administered to patients externally or internally, being administered locally, into a body cavity, into an organ, into the blood circulation, into the respiratory pathway, into the gastrointestinal tract or into the urinogenital tract, or intramuscularly or subcutaneously.

The novel vector can be used to funnel an effector gene into a target cell in a non-cell-specific or cell-specific manner, with the effector gene preferably being a gene which encodes a pharmacologically active compound or an enzyme which cleaves an inactive precursor of an active compound into an active compound. The effector gene can be selected such that the pharmacologically active compound or the enzyme is expressed together with a ligand as a fusion protein, and this ligand binds to the surface of cells, e.g. proliferating endothelial cells or tumor cells.

The present invention also relates to yeast or mammalian cells into which a nucleic acid construct has been inserted using the novel LMW PEI. In a particularly preferred embodiment, the novel LMW PEI is used to introduce the nucleic acid constructs into cell lines which, after having been transfected, can then be used for expressing the transgene.

These cells can consequently be used for preparing a drug for patients. A preferred use of the novel LMW PEI, in a complex with a nucleic acid construct, is that of treating a disease, with the preparation of the drug comprising the insertion of the nucleic acid construct into a target cell and the expression of the construct in a virus-specific or target-cell-specific or metabolically specific or nonspecific and cell-cycle-specific manner.

The invention furthermore relates to the administration of mammalian cells, into which a nucleic acid construct has been inserted using the novel LMW PEI, for preparing a drug for treating a disease. For example, endothelial cells can be isolated from blood, treated in vitro with the novel vector and then, for example, injected intravenously into the patient.

Such cells, which have been transfected in vitro, can also be administered to patients in combination with a novel vector. This combination comprises the cells and vectors each being administered or injected simultaneously or at different times and at the same or at different sites.

EXAMPLES

1) Methods
a) Preparation of Low Molecular Weight Polyethylenimine (LMW PEI)

LMW PEI is obtained from aziridine by a ring-opening polymerization in aqueous solution using acid catalysis. For this, a 10% strength ethylenimine monomer solution in water (5 ml of ethylenimine monomer +45 ml of distilled water, dissolution with stirring) was, for example, stirred at 50° C. for 4 days in the added presence of 1% (0.5 ml) of concentrated hydrochloric acid (37%) as catalyst, then subjected to rotary evaporation and dried at room temperature in vacuo. The molecular weight determinations were carrried out by means of laser scattered light measurement (Wyatt Dawn DSP dispersion photometer) at 633 nm following direct injection into a K5 measuring cell. The molar masses are determined on the basis of the calibration constants determined in toluene and the known initial sample weight.

The molecular weight determination by means of dispersion analysis gave a value of 2000 Da. By comparison, the PEI which was obtained commercially (from Fluka, Neu Ulm) had a molecular weight by dispersion analysis of 791 kDa (HMW PEI).

The two preparations (LMW PEI and HMW PEI) were tested in comparison.

b) Preparation of the Polynucleotide Complexes

The plasmid DNA is complexed with the PEIs following the method of Boussif et al. [Boussif et al., Proc. Natl. Acad. Sci. 92: 7297-7301 (1995)]. 9 mg of the 50% commercial HMW PEI solution or 9 mg of LMW PEI were dissolved in 9 ml of double distilled water and this solution was adjusted to pH 7.4 with 1 N HCl and made up with water to a final volume of 10.0 ml. The completed solutions were sterilized by filtration (0.2 μm) and could be stored for a relatively long period at 4° C.

For complex formation, 10 μg of plasmid and the different quantities of the PEI stock solutions were in each case diluted in 150 mM NaCl to a final volume of 250 μl and mixed in a vortex. Table 1 gives an overview of the mixing and equivalent ratios of the complexes. After a 10-minute incubation at room temperature, the polymer solutions were added dropwise and in portions to the plasmid solutions and mixed in a vortex. The complexes were incubated for a further 10 min before they were added to the cell culture medium.

c) Agarose Shift Assay

The plasmid-binding capacity of the different PEIs was checked in agarose gel shift assays. For this, 1.35-27 μg of HMW PEI and 2.7-90 μg of LMW PEI were in each case complexed with 10 μg of plasmid (Tab. 1). 50 μl aliquots were loaded onto a 1% (w/v) agarose gel of approx. 0.5 cm thickness and developed for 2 h at 80 mV in Tris-EDTA buffer, pH 7.4. The location of the DNA was visualized at 254 nm after reaction with ethidium bromide.

In order to displace-the plasmids from the complexes, 50 μl or 100 μl of a dextran sulfate solution (Mw 5000, 10 mg/ml, Sigma, Deisenhofen) were added to in each case 10 μg of DNA complex 30 min after the complex had been formed.

d) Cell Cultures

L929 mouse fibroblasts were cultured under the standard conditions with which the skilled person is familiar. These cells were sown in 96-well cell culture plates at a density of 8000 cells/well and cultured for 24 h before they were used for toxicity experiments.

3T3 fibroblasts were likewise cultured under standard conditions.

ECV 304 (ATCC, Rockville, Md. USA), which is a spontaneously transformed, adherent human endothelial cell line which was established from apparently normal umbilical cord, was cultured in Dulbecco's modified Eagle's medium (DMEM) (Gibco, Eggenstein) containing 5% fetal calf serum (FCS), 5% horse serum and 1% N-acetyl-L-alanyl-L-glutamine (all from Gibco, Eggenstein).

The cells, which were incubated at 37° C., 95% relative atmospheric humidity and 5% $CO_2$, were passaged twice a week, after having reached confluence, using trypsin/EGTA solution (2.5% stock solution of trypsin, 50 mM solution of ethylene glycol tetraacetic acid, PBS, pH 7.4, in a ratio of 1:1:8). Since the cells detached from the substratum in cell clusters rather than individually, a ⅛ passage was carried out in each case. Cerebral capillary endothelial cells were isolated and cultured in accordance with the method of Bowman et al. [19] and Mischek et al. [Mischek et al., Cell. Tiss. Res. 256: 221-226 (1989)]. For transfection experiments, they were sown in 6-well cell culture plates immediately after having been isolated and cultured up to approx. 50% confluence.

e) Cytotoxicity Study

The toxicity of the polymers was determined on L929 mouse fibroblasts using the MTT assay in accordance with the method of Mosmann et al. [Mosmann, J. Immunol. Methods 65: 55-63 (1983)]. The polymer dilution series were prepared in DMEM containing 10% FCS and 2 mM glutamine and sterilized by filtration (0.2 μm, Schleicher & Schuell, Dassel). The pH and osmolarity of the solutions were corrected if required. After a pre-incubation of 24 h, the cells were treated with the polymer solutions and incubated for 1, 3, 12 and 24 h. The viability of the cells was quantified UV-photometrically by measuring the formazan concentration.

In a second series of experiments, the cells were generally only treated with the polymers for 1 h, after which they were washed and then cultured for a further 3, 12 and 24 h in PEI-free cell culture medium. The evaluation was carried out as described above.

f) Transfections

The ECV 304 cells and 3T3 mouse fibroblasts, which were sown in 3 cm² Petri dishes, and the primary endothelial cells, which were sown in 6-well culture plates, were washed with PBS, pH 7.4, immediately before the experiments and provided with new, serum-supplemented medium. The HMW PEI and LMW PEI complexes, corresponding to 3.33 μg of DNA per well or dish, were added and incubated at 37° C. for 1 hour. The cells were subsequently incubated for 60 hours and the luciferase or β-galactosidase activity was determined in analogy with the manufacturer's instructions. [The HMW PEI and LMW PEI complexes are the corresponding vectors; they contain HMW PEI and LMW PEI, respectively, and nucleic acids, in this case plasmid DNA].

Example 2

Results a) Physicochemical Properties of the PEIs

The behavior of the polymers with regard to their reaction in the endosomal/lysosomal compartment was elucidated by means of swelling studies which were carried out in 0.1 M phosphate buffer at different pH values in the range 4-10. While HMW PEI dissolved at pH 9 and pH 10 to form a clear solution without any residue, an intense turbidity was to be seen at pH 8 and below. This turbidity was largely stable at pH 7 and pH 8. Signs of sedimentation only appeared after several hours. By contrast, a sediment, which was easy to resuspend, was formed within 30 min at pH values in the acid range. Under the same conditions, LMW PEI did not give rise to any turbidity or precipitation but formed a clear solution.

b) Cytotoxicity Studies

The toxicity of the PEIs was determined in vitro on L929 mouse fibroblasts, which various standard organizations recommend as the standard cell culture model for determining the cytotoxicity and biocompatibility of polymers. A direct, linear proportionality between the absorption of the formazan which was formed and the cell number in the range $1 \times 10^3$ and $3 \times 10^4$ cells had been established in preceding experiments. Following a 24-hour growth phase, 8000 cells/well were treated with the polymer solutions and incubated for 1, 3, 12 and 24 h. In the range of 0-1.0 mg/ml, the observed toxic effects of the HMW PEI and the LMW PEI were time- and concentration-dependent over a period of up to 24 h, with the cytotoxicity profiles of the high and low molecular weight PEIs showing marked differences. Thus, in the case of the HMW PEI, the $IC_{50}$ was between 0.06 mg/ml (1 h incubation) and 0.04 mg/ml (24 h incubation), whereas LMW PEI concentrations of between 0.1 and 1.0 mg/ml only became toxic after 12 hours of incubation, with it only being possible to determine an $IC_{50}$ value, which was approximately 0.1 mg/ml, after an incubation period of 24 h.

c) Agarose Gel Shift Assay

In order to ascertain the optimum binding and quantity ratios between plasmid and PEI, a constant quantity of plasmid (10 μg) was complexed as directed with different concentrations of HMW PEI and LMW PEI and then analyzed electrophoretically. Table 1 gives an overview of the mixing ratio of the complexes investigated, the volume of the stock solution used and the absolute quantity of PEI.

TABLE 1

Overview of the mixing ratios of the complexes which contained a) HMW PEI and b) LMW PEI and which were used for the electrophoresis and transfection

| a) Mixing ratio Plasmid/HMW PEI [equivalents] | Volume of the stock solution [μl] | HMW PEI absolute quantity [μg] |
|---|---|---|
| 1 + 1 | 3 | 1.35 |
| 1 + 6.67 | 20 | 9 |

TABLE 1-continued

| | | |
|---|---|---|
| 1 + 10 | 30 | 13.5 |
| 1 + 13.33 | 40 | 18 |
| 1 + 20 | 60 | 27 |

| b) Mixing ratio Plasmid/LMW PEI [equivalents] | Volume of the stock solution [μl] | LMW PEI absolute quantity [μg] |
|---|---|---|
| 1 + 2 | 3 | 2.7 |
| 1 + 13.33 | 20 | 18 |
| 1 + 20 | 30 | 27 |
| 1 + 26.67 | 40 | 36 |
| 1 + 40 | 60 | 54 |
| 1 + 53.33 | 80 | 72 |
| 1 + 66.66 | 100 | 90 |

The location of the plasmids and their complexes was visualized by staining with ethidium bromide. The DNA formed two fluorescent bands which corresponded to the supercoiled and circular forms of the plasmid and which migrated in the direction of the anode. HMW PEI and LMW PEI were not detectable with ethidium bromide.

Complexing DNA with HMW PEI in the ratio of 1+1 resulted in a partial, but still incomplete, retardation of the plasmid at the loading site. Reducing the total loading and/or increasing the diameter prevented the resulting complex from migrating in the gel matrix.

Complexes in the ratio 1+6 to 1+20 were not detectable since they did not exhibit any fluorescence; this indicated that ethidium bromide was excluded from the plasmids because their structure had been efficiently condensed and physically compressed by the HMW PEI. In the case of these complexes, the anion/cation ratios vary from 1:1.2 (1+6) to 1:4 (1+20). Consequently, the complexes should possess a positive overall charge.

2.7 μof LMW PEI were able to almost completely bind and retard 10 μg of plasmid. However, the complex still had a negative overall charge and migrated toward the anode. However, complete cationization and condensation of the DNA was only observed with 54 μg of LMW PEI and above.

In order to verify the effect of the condensation by high and low molecular weight PEI, the DNA was displaced from the completed complexes with an excess of dextran sulfate, which enters into a competitive reaction with the cationic polymers. Both in the case of the HMW PEI and in that of the LMW PEI, it was possible for the DNA to be released once again from the complexes and for all or part of the DNA to migrate into the gel matrix. It was once again possible for ethidium bromide to intercalate and for the DNA therefore to be detectable by fluorescence.

d) In-vitro Transfection Efficiency

The transfection efficiency of the PEI complexes was determined both with cell lines (3T3 mouse fibroblasts and the human endothelial cell line ECV304) and with primary cultures (pig brain capillary endothelial cells).

The commercially available pGL3 control vector from Promega, which carries a luciferase gene under the control of an SV 40 promoter and enhancer, was used as the reporter gene. The ratios in which the plasmid and polymer were mixed in the complexes were the same as those which were used for the electrophoresis.

Concentrations of from 1.35 μg to 27 μg of HMW PEI/10 μg of DNA were tested. Maximum transfection was obtained with 18 μg of HMW PEI. Further increase in the polymer concentration only led to a relatively minor decrease in luciferase expression.

Concentrations of 20-80 μg of LMW PEI/10 μg of DNA were tested in the case of the LMW PEI. In contrast to the situation with HMW PEI, a steady increase in transfection efficiency was detected in the ECV cells as the concentration of LMW PEI increased. At 80 μg of LMW PEI/10 μg of DNA, a reporter gene activity was measured which was approximately 100-fold higher than that obtained when using the dose of 18 μg of HMW PEI/10 μg DNA, which was that which exhibited the maximum activity. Furthermore, no decline in luciferase expression, as occurred with the high molecular weight PEI, was observed even with the highest concentrations of LMW PEI. The experiments with ECV cells and the 3T3 cells gave identical results.

For comparison, the transfection studies using β-galactosidase as the reporter gene were also carried out on endothelial primary cell cultures and using the maximum tolerable, non-cytotoxic doses (MTD) of the HMW PEI and LMW PEI complexes. The in-vitro MTD values were 13.5 μg of HMW PEI/10 μg of DNA and 90 μg of LMW PEI/10 μg of DNA. It was barely possible to transfect cultured pig brain capillary endothelial cells which were incubated with complexes composed of 10 μg of DNA and 13.5 μg of HMW PEI. Only 2-3 cells per culture well displayed the characteristic blue coloration in the region of the cell nuclei. Less than 1% of the treated cells were successfully transfected. By contrast, incubation with complexes composed of 90 μg of LMW PEI and 10 μg of DNA led to significant expression of the marker protein in the endothelial cells. The proportion by percent of blue-stained cells per culture well in relation to the total cell number, i.e. the transfection success rate, was between 5% and 10%. In no case was it possible to observe by light microscopy that the polymer/DNA complexes had any toxic effects on the cells.

The invention claimed is:

1. A single polymerization step process for preparing a branched low molecular weight polyethylenimine (LMW PEI) having a molecular weight of from 500 to about 2,000 Da, which consists of:
   adding hydrochloric acid to an aqueous solution of monomeric ethylenimine, wherein
   (a) the aqueous solution is from 0.1% strength to 90% strength with respect to monomeric ethylenimine and from 0.1% strength to 10% strength with respect to concentrated hydrochloric acid;
   (b) the polymerization is carried out at a reaction temperature of from 30° C. to 70° C.; and
   (c) the reaction time is from 1 to 30 days.

2. The process as claimed in claim 1, wherein the aqueous solution is 10% strength with respect to monomeric ethylenimine and is 1% strength with respect to concentrated hydrochloric acid and wherein the polymerization is carried out at a reaction temperature of 50° C.

3. The process as claimed in claim 2, wherein the reaction time is 4 days.

4. The process as claimed in claim 1, wherein the aqueous solution is 10% strength with respect to monomeric ethylenimine and is 1% strength with respect to concentrated hydrochloric acid and wherein the polymerization is carried out at a reaction temperature of 50° C. and the reaction time is 4 days.

5. The single polymerization step process of claim 2, wherein the LMW PEI has a molecular weight of about 2,000 Da.

6. The single polymerization step process of claim 4, wherein the LMW PEI has a molecular weight of about 2,000 Da.

7. The single polymerization step process of claim 2, wherein the LMW PEI is able to insert a nucleic acid into a cell when the LMW PEI is combined with a nucleic acid.

8. The single polymerization step process of claim 6, wherein the LMW PEI is able to insert a nucleic acid into a cell when the LMW PEI is combined with a nucleic acid.

* * * * *